(12) United States Patent
Cordi et al.

(10) Patent No.: US 8,173,644 B2
(45) Date of Patent: May 8, 2012

(54) 3-SUBSTITUTED-[1,2,3]-BENZOTRIAZINONE COMPOUND FOR ENHANCING GLUTAMATERGIC SYNAPTIC RESPONSES

(75) Inventors: Alexis Cordi, Suresnes (FR); Gary Rogers, Basseterre (KN); Rudolf Mueller, Foothill Ranch, CA (US)

(73) Assignee: Les Laboratoires Servier, Suresnes Cedex (FR)

( * ) Notice: Subject to any disclaimer, the term of this patent is extended or adjusted under 35 U.S.C. 154(b) by 164 days.

(21) Appl. No.: 12/448,784

(22) PCT Filed: Dec. 28, 2007

(86) PCT No.: PCT/US2007/026416
§ 371 (c)(1),
(2), (4) Date: Sep. 29, 2009

(87) PCT Pub. No.: WO2008/085506
PCT Pub. Date: Jul. 17, 2008

(65) Prior Publication Data
US 2010/0137295 A1    Jun. 3, 2010

Related U.S. Application Data

(60) Provisional application No. 60/878,503, filed on Jan. 3, 2007, provisional application No. 60/921,433, filed on Apr. 2, 2007.

(51) Int. Cl.
*C07D 498/04* (2006.01)
*A61K 31/5365* (2006.01)
(52) U.S. Cl. .................................. 514/229.8; 544/89
(58) Field of Classification Search ............. 544/89; 514/229.8
See application file for complete search history.

(56) References Cited

U.S. PATENT DOCUMENTS

| | | | |
|---|---|---|---|
| 3,723,436 | A | 3/1973 | Hollstein et al. |
| 4,797,482 | A | 1/1989 | Constansa et al. |
| 5,650,409 | A | 7/1997 | Rogers et al. |
| 5,736,543 | A | 4/1998 | Rogers et al. |
| 5,747,492 | A | 5/1998 | Lynch et al. |
| 5,783,587 | A | 7/1998 | Rogers et al. |
| 5,962,447 | A | 10/1999 | Rogers et al. |
| 6,030,968 | A | 2/2000 | Gall et al. |
| 6,303,542 | B1 | 10/2001 | Li et al. |
| 2002/0055508 | A1 | 5/2002 | Rogers et al. |
| 2003/0153752 | A1 | 8/2003 | Hirst et al. |
| 2005/0026952 | A1 | 2/2005 | Mathias |
| 2005/0148603 | A1 | 7/2005 | Jimenez et al. |
| 2010/0041647 | A1 | 2/2010 | Mueller et al. |
| 2010/0120764 | A1 | 5/2010 | Street et al. |

FOREIGN PATENT DOCUMENTS

| | | |
|---|---|---|
| DE | 2012094 | 9/1971 |
| WO | WO9402475 | 2/1994 |
| WO | 9736907 | 10/1997 |
| WO | 9933469 | 7/1999 |
| WO | WO9942456 | 8/1999 |
| WO | 03099299 A1 | 12/2003 |
| WO | WO 03/099299 | 12/2003 |
| WO | 2008085505 A1 | 7/2008 |
| WO | 2008143963 A1 | 11/2008 |
| WO | 2009023126 A2 | 2/2009 |
| WO | 2009038752 A2 | 3/2009 |

OTHER PUBLICATIONS

Murray et al., LY503430, a novel AMPA receptor potentiator with functional, neuroprotective and neurotrophic effects in rodent models of Parkinson's disease. J. Pharmacol. Exp. Ther. 2003, vol. 306, pp. 752-762.
Russell, Increased AMPA Receptor Function in Slices Containing the Prefrontal Cortex of Spontaneously Hypertensive Rats. Metabolic Brain Disease, 2001, vol. 16, pp. 143-149.
Pontarelli, New drug that enhances glutamate transmission in brain being evaluated for fragile X, 2002, downloaded Oct. 4, 2008, URL:http://www.innovations-report.com/html/reports/medicine_health/report-12386.html.
Gouaux et al.,Structure and function of AMPA receptors. J. Physiol. 2003, 554, 249-253.
Gueyrard et al. A new and rapid access to homochiral 2,3-dihydro-oxazolo[2,3-b]quinazolin-5-ones, Tetrahedron: Assymmetry 2001, 12, 337-340.
Murray et al. LY503430, a novel AMPA receptor potentiator with functional, neuroprotective and neurotrophic effects in rodent models of Parkinson's disease. J. Pharmacol. Exp. Ther. 2003, 306, 752-762.
Russell, Increased AMPA Receptor Function in Slices Containing the Prefrontal Cortex of Spontaneously Hypertensive Rats. Metabolic Brain Disease, 2001, 16, 143-149.
Pontarelli, New drug that enhances glutamate transmission in brain being evaluated for fragile X. printed Apr. 10, 2008 from Http://www.innovations-report.com/html/reports/medicine_health/report-12386.html.
Ren. Ampakines alleviate respiratory depression in rats. American Journal of Respiratory and Critical Care Medicine 2006, 174, 1384-1391.
Monaghan et al., In Brain Research 324:160 164 (1984).
Arai and Lynch, Brain Research 598:173 184 (1992).
Granger et al., Synapse 15:326 329 (1993).
Staubli et al., PNAS 91:777-781 (1994).
Arai et al., Brain Res. 638:343 346 (1994).
Staubli et al., PNAS 91:11158-11162 (1994).
Shors et al., Neurosci. Let. 186:153 156 (1995).
Larson et al., J. Neurosci. 15:8023 8030 (1995).
Granger et al., Synapse 22:332 337 (1996).
Arai et al., JPET 278:627 638 (1996).
Lynch et al., Internat. Clin. Psychopharm. 11: 13 19 (1996).
Lynch et al., Exp. Neurology 145:89-92 (1997).
Ingvar et al., Exp. Neurology 146:553-559 (1997).

(Continued)

*Primary Examiner* — Kahsay T Habte
(74) *Attorney, Agent, or Firm* — Hueschen and Sage

(57) ABSTRACT

This invention relates to the prevention and treatment of cerebral insufficiency, including enhancement of receptor functioning in synapses in brain networks responsible for higher order behaviors. These brain networks are involved in cognitive abilities related to memory impairment, such as is observed in a variety of dementias, an in imbalances in neuronal activity between different brain regions, as is suggested in disorders such as Parkinson's disease, schizophrenia and affective disorders. In a particular aspect, the present invention relates to a compound useful for treatment of such conditions, and methods of using this compound for such treatment.

7 Claims, No Drawings

OTHER PUBLICATIONS

Hampson, et al., J. Neurosci. 18:2748-2763 (1998).
Porrino et al., PLoS Biol 3(9):1-14 (2006).
del Cerro and Lynch, Neuroscience 49: 1 6 (1992).
Whitlock et al., Science 313:1093-1097 (2006).
Pastalkova, et al., Science 313:1141-1144 (2006).
Rex, et al., J. Neurophysiol. 96:677-685 (2006).
Lauterborn, et al., J. Neurosci. 20:8-21 (2000).
Lauterborn, et al., JPET 307:297-305 (2003).
Mackowiak, et al., Neuropharmacology 43:1-10 (2002).
O'Neill, et al., Eur. J. Pharmacol. 486:163-174 (2004).
Kent, et al., Mol. Psychiatry 10:939-943 (2005).
Riikonen, et al., J. Child Neurol. 18:693-697 (2003).
Chang, et al., Neuron 49:341-348 (2006).
Ito et al., J. Physiol. 424:533 543 (1990).
Staubli et al., Psychobiology 18:377 381 (1990).
Xiao et al., Hippocampus 1:373 380 (1991).
Guenzi and Zanetti, J. Chromatogr. 530:397 406 (1990).
Himori, et al., Pharmacology Biochemistry and Behavior 47:219-225 (1994).
Pizzi et al., J. Neurochem. 61:683-689 (1993).
Nakamura and Shirane, Eur. J. Pharmacol. 380: 81-89 (1999).
Spignoli and Pepeu, Pharmacol. Biochem. Behay. 27:491-495 (1987).
Hall and Von Voigtlander, Neuropharmacology 26:1573-1579(1987).
Kessler et al., Brain Res. 560: 337 341 (1991).
Staubli et al., Hippocampus 2: 4958 (1992).
Sirvio et al., Neuroscience 74: 1025-1035 (1996).
Chapter 7, Neuroscience, edited by Dale Purves, Sinauer Associates, Inc., Sunderland, MA 1997.
Advokat, et al., Neurosci. Biobehav. Rev., 1992, 16, 13-24.
Artero, et al., Acta. Psychiatri. Scand., 2003, 107, 390-393.
Bai, et al., Neuropharmacol., 2003, 44, 1013-1021.
Beneyto, et al., Neuropsychopharmacol., 2007, 32, 1888-1902.
Bernard, et al., CNS Neurosci. Ther., 2010, 16, 193-212.
Black, Psychopharmacology, 2005, 179, 154-163.
Bliss, et al., Nature, 1993, 361, 31-39.
Chappell, et al., Neurology, 2007, 68, 1008-1012.
Destot-Wong, et al., Neuropharmacol., 2009, 57, 277-286.
Dicou, et al., Brain Res., 2003, 970, 221-225.
Ehlers, et al., Neuron, 2007, 54, 447-460.
Hammond, et al., Neuropsychopharmacol., 2010, 35, 2110-2119.
Heine, et al., Science, 2008, 320, 201-205.
Huntley, et al., Int. J. Geriatr. Psychiatry, 2010, 25, 121-132.
Lambon, et al., Brain, 2003, 126, 2350-2362.
Lockhart, et al., Eur. J. Pharmacol., 2007, 561, 23-31.
Lynch, Curr. Opin. Pharmacol., 2006, 6, 82-88.
Lynch, et al., Trends Neurosci., 2006, 29, 554-562.
Malenka, et al., NY Acad. Sci., 2003, 1003, 1-11.
Manji, et al., Psychiatry, 2003, 53, 707-742.
O'Neill, et al., Curr. Drug Targets, 2007, 8, 603-620.
O'Neill, et al., Idrugs, 2007, 10, 185-192.
Palmer, et al., Pharmacol. Rev., 2005, 57, 253-277.
Rapp, et al., Curr. Opin. Neurol., 1994, 7, 294-298.
Robbins, et al., Trends, Pharmacol. Sci., 2006, 27, 141-148.
Roger, et al., 9th Int. Conf. on Alzheimer's Disease & Related Disorders, Philadelphia 2004.
Sanacora, et al., Nat. Rev. Drug Discov., 2008, 7, 426-437.
Schinder, et al., Trends Neurosci., 2000, 23, 639-645.
Shimamura, Seminar Neurosci., 2000, 23, 639-645.
Simmons, et al., Neurogbiol. Aging, 2011, 41, 436-444.
Simmons, et al., Proc. Nat. Acad. Sci., 2009, 105, 4906-4911.
Su, et al., Psychopharmacol., 2009, 206, 215-222.
Voss, et al., Neuropharmacol., 2007, 52, 590-597.
Whitlock, et al., Science, 2006, 313, 1093-1097.
Wollmuth, et al., Trends Neurosci., 2004, 27, 321-328.

3-SUBSTITUTED-[1,2,3]-BENZOTRIAZINONE COMPOUND FOR ENHANCING GLUTAMATERGIC SYNAPTIC RESPONSES

RELATED APPLICATIONS

This application claims the benefit of priority of U.S. provisional applications U.S. 60/878,503, filed Jan. 3, 2007 and U.S. 60/921,433, filed Apr. 2, 2007, relevant portions of which applications are incorporated by reference herein.

FIELD OF THE INVENTION

This invention relates to a compound, pharmaceutical compositions and methods for use in the prevention and treatment of cerebral insufficiency, including enhancement of receptor functioning at synapses in brain networks responsible for higher order behaviors. These brain networks, which are involved in cognitive abilities, are related to memory impairment, such as is observed in ageing and a variety of dementias, in imbalances in neuronal activity between different brain regions, as is suggested in disorders such as Parkinson's disease, schizophrenia, attention deficit and affective or mood disorders, and in disorders wherein a deficiency in neurotrophic factors is implicated. In a particular aspect, the present invention relates to compounds useful for treatment of such conditions, and methods of using these compounds for such treatment.

BACKGROUND OF THE INVENTION

The release of glutamate at synapses at many sites in mammalian forebrain stimulates two classes of postsynaptic, ionotropic receptors. These classes are usually referred to as AMPA/quisqualate and N-methyl-D-aspartic acid (NMDA) receptors. AMPA/quisqualate receptors mediate a voltage independent fast excitatory post-synaptic current (the fast EPSC), whereas NMDA receptors generate a voltage-dependent, slow excitatory current. Studies carried out in slices of hippocampus or cortex, indicate that the AMPA receptor mediated fast EPSC is generally the dominant component by far at most glutamatergic synapses.

AMPA receptors are not evenly distributed across the brain but rather are largely restricted to the telencephalon and cerebellum. These receptors are found in high concentrations in the superficial layers of neocortex, in each of the major synaptic zones of hippocampus, and in the striatal complex, as reported by Monaghan et al., in *Brain Research* 324:160-164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that modulate and thereby enhance the functioning of AMPA receptors could have significant benefits for cognitive and intellectual performance. Such drugs should also facilitate memory encoding. Experimental studies, such as those reported by Arai and Lynch, *Brain Research* 598:173-184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

Compounds that enhance the functioning of the AMPA form of glutamate receptors facilitate the induction of LTP and the acquisition of learned tasks in rodents and humans as measured in a number of paradigms. See, for example, Granger et al., *Synapse* 15:326-329 (1993); Staubli et al., *PNAS* 91:777-781 (1994); Arai et al., Brain Res. 638:343-346 (1994); Staubli et al., *PNAS* 91:11158-11162 (1994); Shors et al., *Neurosci. Let.* 186:153-156 (1995); Larson et al., *J. Neurosci.* 15:8023-8030 (1995); Granger et al., *Synapse* 22:332-337 (1996); Arai et al., *JPET* 278:627-638 (1996); Lynch et al., *Internat. Clin. Psychopharm.* 11: 13-19 (1996); Lynch et al., *Exp. Neurology* 145:89-92 (1997); Ingvar et al., *Exp. Neurology* 146:553-559 (1997); Hampson, et al., *J. Neurosci.* 18:2748-2763 (1998); Porrino et al., PLoS Biol 3(9):1-14 (2006) and Lynch and Rogers, U.S. Pat. No. 5,747,492. There is a considerable body of evidence showing that LTP is a substrate of memory. For example, compounds that block LTP interfere with memory formation in animals, and certain drugs that disrupt learning in humans antagonize the stabilization of LTP, as reported by del Cerro and Lynch, *Neuroscience* 49: 1-6 (1992). Learning a simple task induces LTP in hippocampus that occludes LTP generated by high frequency stimulation (Whitlock et al., Science 313:1093-1097 (2006)) and a mechanism that maintains LTP sustains spatial memory (Pastalkova, et al., Science 313:1141-1144 (2006)). Of significant importance to the field of learning is the finding that in vivo treatments with a positive AMPA-type glutamate receptor modulator restores stabilization of basal dendritic LTP in middle-aged animals (Rex, et al., *J Neurophysiol.* 96:677-685 (2006)).

Excitatory synaptic transmission provides a major pathway by which neurotrophic factors are increased within specific brain regions. As such, potentiation of AMPA receptor function by modulators has been found to increase levels of neurotrophins, particularly brain derived neurotrophic factor, or BDNF. See, for example, Lauterborn, et al., *J. Neurosci.* 20:8-21 (2000); Gall, et al., U.S. Pat. No. 6,030,968; Lauterborn, et al., JPET 307:297-305 (2003); and Mackowiak, et al., *Neuropharmacology* 43:1-10 (2002). Other studies have linked BDNF levels to a number of neurological disorders, such as Parkinson's disease, Attention Deficit Hyperactivity Disorder (ADHD), autism, Fragile-X Syndrome, and Rett Syndrome (RTT). See, for example, O'Neill, et al., *Eur. J. Pharmacol.* 486:163-174 (2004); Kent, et al., *Mol. Psychiatry.* 10:939-943 (2005); Riikonen, et al., *J. Child Neurol.* 18:693-697 (2003) and Chang, et al., *Neuron* 49:341-348 (2006). Thus, AMPA receptor potentiators may be useful for the treatment of these, as well as other, neurological diseases that are the result of a glutamatergic imbalance or a deficit in neurotrophic factors.

A prototype for a compound that increases AMPA receptor function was described by Ito et al., *J. Physiol.* 424:533-543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials (Staubli et al., *Psychobiology* 18:377-381 (1990) and Xiao et al., *Hippocampus* 1:373-380 (1991)).

Aniracetam has been found to have an extremely rapid onset and washout, and can be applied repeatedly with no apparent lasting effects, which are desirable features for behaviorally-relevant drugs. Aniracetam does present several disadvantages, however. The peripheral administration of aniracetam is not likely to influence brain receptors. The drug works only at high concentrations (approx. 1000 μM), and about 80% of the drug is converted to anisoyl-GABA following peripheral administration in humans (Guenzi and Zanetti, *J. Chromatogr.* 530:397-406 (1990)). The metabolite, anisoyl-GABA, has been found to have less synaptic activity than aniracetam. In addition to these issues, aniracetam has putative effects on a plethora of other neurotransmitter and enzymatic targets in the brain, which makes uncertain the mechanism of any claimed therapeutic drug effect. See, for example, Himori, et al., *Pharmacology Biochemistry and Behavior* 47:219-225 (1994); Pizzi et al., *J. Neurochem.* 61:683-689 (1993); Nakamura and Shirane, *Eur. J. Pharmacol.* 380: 81-89 (1999); Spignoli and Pepeu, *Pharmacol. Biochem. Behav.* 27:491-495 (1987); Hall and Von Voigtlander, *Neuropharmacology* 26:1573-1579 (1987); and Yoshimoto et al., *J. Pharmacobiodyn.* 10:730-735 (1987).

A class of AMPA receptor-modulating compounds that does not display the low potency and inherent instability characteristic of aniracetam has been described (Lynch and Rogers, U.S. Pat. No. 5,747,492). These compounds, termed "Ampakines"®, can be substituted benzamides, which include, for example, 1-(quinoxaline-6-ylcarbonyl)piperidine (CX516; Ampalex®). Typically, they are chemically more stable than aniracetam and show improved bioavailability. CX516 is active in animal tests used to detect efficacious drugs for the treatment of memory disorders, schizophrenia, and depression. In three separate clinical trials, CX516 showed evidence for efficacy in improving various forms of human memory (Lynch et al., *Internat. Clin. Psychopharm.* 11:13-19 (1996); Lynch et al., *Exp. Neurology* 145:89-92 (1997); Ingvar et al., *Exp. Neurology* 146:553-559 (1997)).

Another class of Ampakines, benzoxazines, has been discovered to have very high activity in in vitro and in vivo models for assessing the probability of producing cognition enhancement (Rogers and Lynch; U.S. Pat. No. 5,736,543). The substituted benzoxazines are rigid benzamide analogues with different receptor modulating properties from the flexible benzamide, CX516.

Certain substituted benzofurazan and benzothiadiazole compounds have been found to be significantly and surprisingly more potent in the animal model of schizophrenia than previous compounds, and are also effective in cognition enhancement. These compounds are structurally similar to those disclosed in Lynch and Rogers, U.S. Pat. No. 5,736,543.

Previously disclosed structures that contained the 1,3-benzoxazine-4-one pharmacophore were substituted on the benzene portion by heteroatoms, such as nitrogen or oxygen (U.S. Pat. Nos. 5,736,543 and 5,962,447), by substituted alkyl groups (U.S. Pat. Nos. 5,650,409 and 5,783,587), or unsubstituted (WO 99/42456). Yet another class of 1,3-benzoxazine compounds contained a carbonyl external to the oxazine ring (U.S. Pat. No. 6,124,278), but not as a substituent on the benzene ring structure. Now, a new class of triazinone compounds has been discovered that display significant activity on hippocampal synaptic responses and neuronal whole cell currents mediated by AMPA receptors. 3-Substituted benzo[1,2,3]triazin-4-one compounds are potent AMPA receptor modulators that are significantly more metabolically stable than the corresponding bis-benzoxazinones.

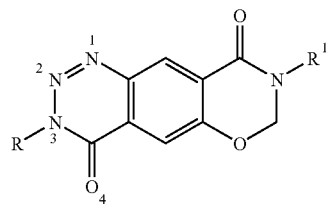

The biological activity of the triazinones was unexpected and the potency at the AMPA receptor is surprisingly high; the most potent triazinones in this class double AMPA receptor currents at concentrations as low as 3 nM. A benzo[1,2,3] triazin-4-one compound as a AMPA receptor modulator is disclosed herein.

SUMMARY OF THE INVENTION

The present invention includes, in one aspect, a compound as shown by structure I, and is described in Section II of the detailed description, which follows. Administration of compounds of this class has been found to increase synaptic responses mediated by AMPA receptors. The compound of the present invention is significantly and unexpectedly more potent than previously described compounds in increasing AMPA receptor function in primary neuronal cultures and in slices of rat hippocampus, and in enhancing cognitive performance, such as performance in a delayed match to sample task. This unexpected activity translates into pharmaceutical compounds and corresponding methods of use, including treatment methods, which utilize significantly lower concentrations (on a mole-to-mole basis) of the present compounds compared to prior art compositions.

The ability of the compound of the invention to increase AMPA receptor-mediated responses makes the compounds useful for a variety of purposes. These include facilitating the learning of behaviors dependent upon glutamate receptors, treating conditions in which AMPA receptors or synapses utilizing these receptors are reduced in numbers or efficiency, and enhancing excitatory synaptic activity in order to restore an imbalance between brain sub-regions or increase the levels of neurotrophic factors.

In another aspect, the invention includes a method for the treatment of a mammalian subject suffering from a hypoglutamatergic condition, or from a deficiency in the number or strength of excitatory synapses, or in the number of AMPA receptors, such that memory or other cognitive functions are impaired. Such conditions may also cause a cortical/striatal imbalance, leading to schizophrenia or schizophreniform behavior. According to the method, such a subject is treated with an effective amount of a compound as shown by structure I, and is described in Section II of the detailed description, following, in a pharmaceutically acceptable carrier.

These and other objects and features of the invention will become more fully apparent when the following detailed description of the invention is read in conjunction with the accompanying drawings.

DETAILED DESCRIPTION OF THE INVENTION

I. Definitions

The terms below have the following definitions unless indicated otherwise. Other terms that are used to describe the present invention have the same definitions as those terms are generally used by those skilled in the art.

The term "alkyl" is used herein to refer to a fully saturated monovalent radical containing carbon and hydrogen, and which may be a straight chain, branched or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl.

The term "alkenyl" is used herein to refer to a monovalent radical containing carbon and hydrogen that contains one or two sites of unsaturation, and which may be a straight chain, branched or cyclic. Examples of alkyl groups are ethenyl, n-butenyl, n-heptenyl, isopropenyl, cyclopentenyl, cyclopentenylethyl and cyclohexenyl.

The term "substituted alkyl" refers to alkyl as just described including one or more functional groups such as lower alkyl containing 1-6 carbon atoms, aryl, substituted aryl, acyl, halogen (i.e., alkyl halos, e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

The term "aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as oxazolyl, isoxazolyl, pyrazolyl, thiazolyl, thiadiazolyl, tetrazolyl, pyridazinyl, pyrimidyl, benzofuryl, benzothienyl, benzimidazolyl, benzoxazolyl, benzothiazolyl, quinolyl, isoquinolyl, imidazolyl, furyl, pyrrolyl, pyridyl, thienyl and indolyl.

The term "substituted" as used in the term "substituted aryl, substituted aromatic, substituted heteroaryl, or substituted heteroaromatic" herein signifies that one or more substituents may be present, said substituents being selected from atoms and groups, which when present do not prevent the compound from functioning as a potentiator of AMPA receptor function. Examples of substituents that may be present in a substituted aromatic or heteroaromatic group include, but are not limited to, groups such as ($C_1$-$C_7$) alkyl, ($C_1$-$C_7$) acyl, aryl, heteroaryl, substituted aryl and heteroaryl, halogen, cyano, nitro, ($C_1$-$C_7$) alkylhalos (e.g., $CF_3$), hydroxy, ($C_1$-$C_7$) alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated ($C_3$-$C_8$) cyclic hydrocarbons, ($C_3$-$C_8$) heterocycles and the like. "Heterocycle" or "heterocyclic" refers to a carbocylic ring wherein one or more carbon atoms have been replaced with one or more heteroatoms such as nitrogen, oxygen or sulfur. Examples of heterocycles include, but are not limited to, piperidine, pyrrolidine, morpholine, thiomorpholine, piperazine, tetrahydropyran, tetrahydropyran, 2-pyrrolidinone, δ-velerolactam, δ-velerolactone and 2-ketopiperazine.

The term "substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

The term "compound" is used herein to refer to any specific chemical compound disclosed herein. Within its use in context, the term generally refers to a single compound, but in certain instances may also refer to stereoisomers and/or optical isomers (including racemic mixtures) of disclosed compounds.

The term "effective amount" refers to the amount of a selected compound of formula I that is used to enhance glutamatergic synaptic response by increasing AMPA receptor activity. The precise amount used will vary depending upon the particular compound selected and its intended use, the age and weight of the subject, route of administration, and so forth, but may be easily determined by routine experimentation. In the case of the treatment of a condition or disease state, an effective amount is that amount which is used to effectively treat the particular condition or disease state.

The term "pharmaceutically acceptable carrier" refers to a carrier or excipient which is not unacceptably toxic to the subject to which it is administered. Pharmaceutically acceptable excipients are described at length by E. W. Martin, in "Remington's Pharmaceutical Sciences."

A "pharmaceutically acceptable salt" of an amine compound, such as those contemplated in the current invention, is an ammonium salt having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like.

The term "patient" or "subject" is used throughout the specification to describe an animal, generally a mammalian animal, including a human, to whom treatment or use with the compounds or compositions according to the present invention is provided. For treatment or use with/or of those conditions or disease states which are specific for a specific animal (especially, for example, a human subject or patient), the term patient or subject refers to that particular animal.

The term "sensory motor problems" is used to describe a problem which arises in a patient or subject from the inability to integrate external information derived from the five known senses in such a way as to direct appropriate physical responses involving movement and action.

The term "cognitive task" or "cognitive function" is used to describe an endeavor or process by a patient or subject that involves thought or knowing. The diverse functions of the association cortices of the parietal, temporal and frontal lobes, which account for approximately 75% of all human brain tissue, are responsible for much of the information processing that goes on between sensory input and motor output. The diverse functions of the association cortices are often referred to as cognition, which literally means the process by which we come to know the world. Selectively attending to a particular stimulus, recognizing and identifying these relevant stimulus features and planning and experiencing the response are some of the processes or abilities mediated by the human brain which are related to cognition.

The term "brain network" is used to describe different anatomical regions of the brain that communicate with one another via the synaptic activity of neuronal cells.

The term "AMPA receptor" refers to an aggregate of proteins found in some membranes, which allows positive ions to cross the membrane in response to the binding of glutamate or AMPA (DL-α-amino-3-hydroxy-5-methyl-4-isoxazolepropionic acid), but not NMDA.

The term "excitatory synapse" is used to describe a cell-cell junction at which release of a chemical messenger by one cell causes depolarization of the external membrane of the other cell. An excitatory synapse describes a postsynaptic neuron which has a reversal potential that is more positive than the threshold potential and consequently, in such a synapse, a neurotransmitter increases the probability that an excitatory post synaptic potential will result (a neuron will fire producing an action potential). Reversal potentials and threshold potentials determine postsynaptic excitation and inhibition. If the reversal potential for a post synaptic potential ("PSP") is more positive than the action potential threshold, the effect of a transmitter is excitatory and produces an excitatory post synaptic potential ("EPSP") and the firing of an action potential by the neuron. If the reversal potential for a post synaptic potential is more negative than the action potential threshold, the transmitter is inhibitory and may generate inhibitory post synaptic potentials (IPSP), thus reducing the likelihood that a synapse will fire an action potential. The general rule for postsynaptic action is: if the reversal potential is more positive than threshold, excitation results; inhibition occurs if the reversal potential is more negative than threshold. See, for example, Chapter 7, *NEUROSCIENCE*, edited by Dale Purves, Sinauer Associates, Inc., Sunderland, Mass. 1997.

The term "motor task" is used to describe an endeavor taken by a patient or subject that involves movement or action.

The term "perceptual task" is used to describe an act by a patient or subject of devoting attention to sensory inputs.

The term "synaptic response" is used to describe biophysical reactions in one cell as a consequence of the release of chemical messengers by another cell with which it is in close contact.

The term "hypoglutamatergic condition" is used to describe a state or condition in which transmission mediated by glutamate (or related excitatory amino acids) is reduced to below normal levels. Transmission consists of the release of glutamate, binding to post synaptic receptors, and the opening of channels integral to those receptors. The end point of the hypoglutamatergic condition is reduced excitatory post synaptic current. It can arise from any of the three above noted phases of transmission. Conditions or disease states which are considered hypoglutamatergic conditions and which can be treated using the compounds, compositions and methods according to the present invention include, for example, loss of memory, dementia, depression, attention disorders, sexual dysfunction, movement disorders, including Parkinson's disease, schizophrenia or schizophreniform behavior, memory and learning disorders, including those disorders which result from aging, trauma, stroke and neurodegenerative disorders, such as those associated with drug-induced states, neurotoxic agents, Alzheimer's disease, and aging. These conditions are readily recognized and diagnosed by those of ordinary skill in the art.

The term "cortico-striatal imbalance" is used to describe a state in which the balance of neuronal activities in the interconnected cortex and underlying striatal complex deviates from that normally found. 'Activity' can be assessed by electrical recording or molecular biological techniques. Imbalance can be established by applying these measures to the two structures or by functional (behavioral or physiological) criteria.

The term "affective disorder" or "mood disorder" describes the condition when sadness or elation is overly intense and continues beyond the expected impact of a stressful life event, or arises endogenously. As used herein, the term "effective disorder" embraces all types of mood disorders as described in, for example, *Diagnostic and Statistical Manual of Mental Disorders*, Fourth Edition (DSM IV), pages 317-391.

The term "schizophrenia" is used to describe a condition which is a common type of psychosis, characterized by a disorder in the thinking processes, such as delusions and hallucinations, and extensive withdrawal of the individual's interest from other people and the outside world, and the investment of it in his or her own. Schizophrenia is now considered a group of mental disorders rather than a single entity, and distinction is made between reactive and process schizophrenias. As used herein, the term schizophrenia or "schizophreniform" embraces all types of schizophrenia, including ambulatory schizophrenia, catatonic schizophrenia, hebephrenic schizophrenia, latent schizophrenia, process schizophrenia, pseudoneurotic schizophrenia, reactive schizophrenia, simple schizophrenia, and related psychotic disorders which are similar to schizophrenia, but which are not necessarily diagnosed as schizophrenia per se. Schizophrenia and other psychotic disorders may be diagnosed using guidelines established in, for example, *Diagnostic and Statistical Manual of Mental Disorders*, Fourth Edition (DSM IV) Sections 293.81, 293.82, 295.10, 295.20, 295.30, 295.40, 295.60, 295.70, 295.90, 297.1, 297.3, 298.8.

The term "brain function" is used to describe the combined tasks of perceiving, integrating, filtering and responding to external stimuli and internal motivational processes.

The term "impaired" is used to describe a function working at a level that is less than normal. Impaired functions can be significantly impacted such that a function is barely being carried out, is virtually non-existent or is working in a fashion that is significantly less than normal. Impaired functions may also be sub-optimal. The impairment of function will vary in severity from patient to patient and the condition to be treated.

II. Compounds that Increase AMPA Receptor Function

The present invention is directed, in one aspect, to a compound having the property of enhancing AMPA receptor function. The specified compound of this invention having the structure I, below:

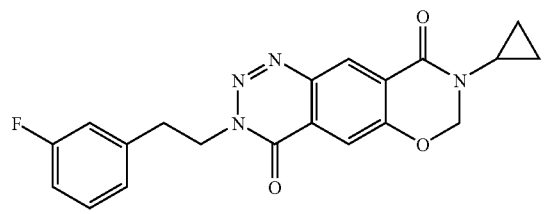

The synthesis of the invention compound, 8-cyclopropyl-3-[2-(3-fluorophenyl)ethyl]-7,8-dihydro-3H-[1,3]oxazino[6,5-g][1,2,3]benzotriazine-4,9-dione, is preferably carried out by the following synthetic scheme, wherein the synthesis of the substituted salicylamide is well-known in the field of organic synthesis:

SCHEME 1

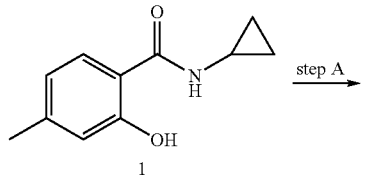

-continued

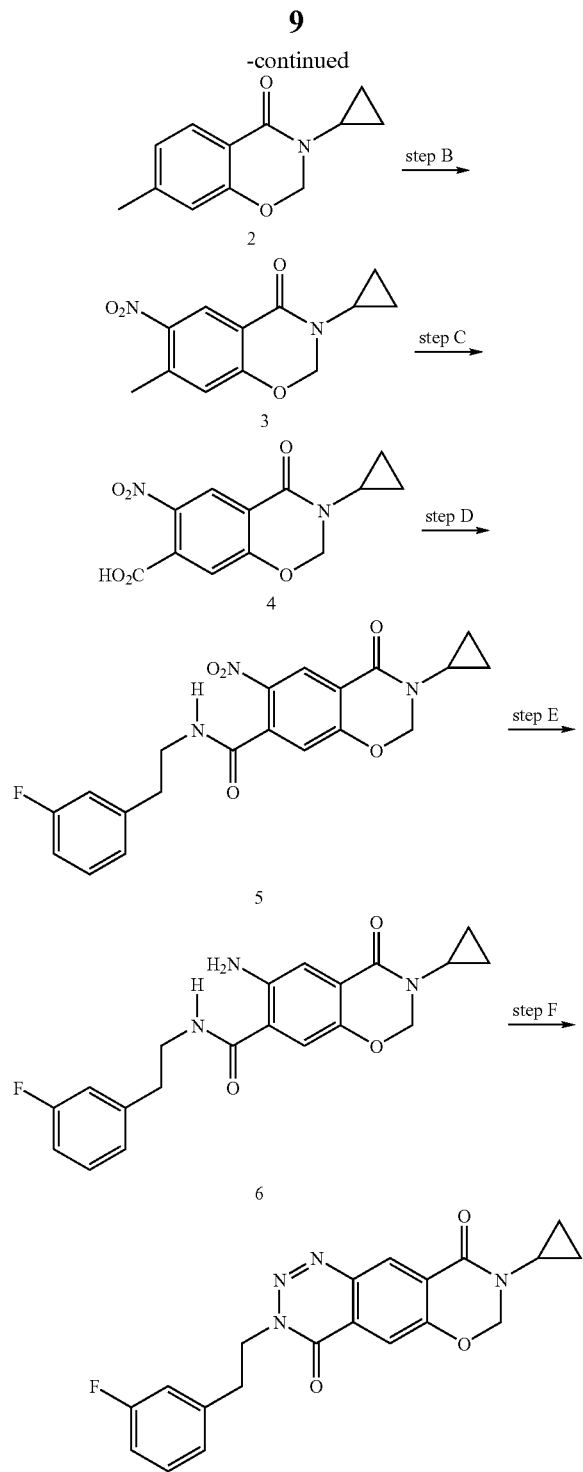

In Scheme 1, step A may be carried out under standard conditions, among them acid catalyzed insertion of a formaldehyde synthon. For example, the salicylamide (1) is dissolved and heated in a suitable organic solvent together with trioxane and sulfuric or hydrochloric acid. Step B is a nitration reaction that can be carried out under mild conditions known to those skilled in organic synthesis and detailed in such volumes at Reagents for Organic Synthesis (Fieser and Fieser) and Organic Syntheses (see web site at http://www.orgsyn.org/). Step C involves the 2-step oxidation of the methyl group of compound 3 to a carboxylic acid via an intermediate aldehyde employing N,N-dimethylformamide dimethyl acetal and sodium periodate followed by oxone. Step D involves coupling of a primary amine to the nitro acid, which can be accomplished using a variety of coupling reagents known to a skilled chemist. Some non-limiting examples commonly used are thionyl chloride, oxalyl chloride or carbonyl diimidazole. Step E is a reduction of an aryl nitro to an aniline and can be effected by reduction using a variety of catalysts including, but not limited to, Pd or Pt or Raney Ni and hydrogen or Zn/Cu. Step F forms the triazinone ring and can be carried out by the addition of isoamyl nitrite in DMF.

All compositions disclosed in the present application may be synthesized by the above-described methods using analogous synthetic steps to those specifically presented in the examples described herein as well as those known in the art. Also claimed are all addition salts with a pharmaceutically acceptable acid or base thereof.

III. Method of Treatment

According to one aspect of the invention, a method is provided for treating a mammalian subject suffering from a hypoglutamatergic condition, or from deficiencies in the number or strength of excitatory synapses or in the number of AMPA receptors. In such a subject, memory or other cognitive functions may be impaired or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present, invention include those disorders that result from aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

In the present invention, the method of treatment comprises administering to the subject in need of treatment, in a pharmaceutically acceptable carrier, an effective amount of 8-cyclopropyl-3-[2-(3-fluorophenyl)ethyl]-7,8-dihydro-3H-[1,3] oxazino[6,5-g][1,2,3]benzotriazine-4,9-dione having the formula:

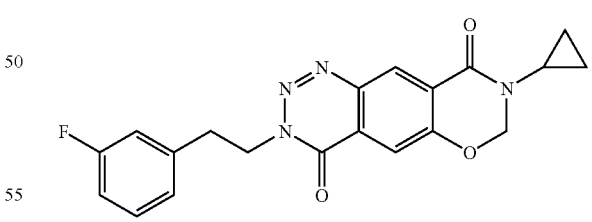

or a pharmaceutically acceptable addition salt of an acid or base thereof.

As noted above, treatment of a subject according to the method of the invention is useful for enhancing AMPA receptor activity, and thus may be used to facilitate the learning of behaviors dependent upon AMPA receptors, and to treat conditions, such as memory impairment, in which AMPA receptors, or synapses utilizing these receptors, are reduced in numbers or efficiency. The method is also useful for enhancing excitatory synaptic activity in order to restore an imbalance between brain sub-regions, which may manifest itself in schizophrenia or schizophreniform behavior, or other behavior as described above. The compounds administered in accordance with the method have been found to be more effective than previously described compounds in enhancing AMPA receptor activity, as shown in the in vitro and in vivo tests described below.

IV. Biological Activity

Enhancement of AMPA Receptor Function

Synaptic responses mediated by AMPA receptors are increased according to the method of the invention, using the compound described herein. The compound is demonstrated to be substantially more potent than previously-described compounds in increasing AMPA mediated whole cell currents in cultured neurons. The in vitro assay is described as follows. Cortical cells were prepared from day 18-19 embryonic Sprague-Dawley rats and recorded after 3 days in culture. The extracellular solution (ECS) contained (in mM): NaCl (145), KCl (5.4), HEPES (10), MgCl2 (0.8), CaCl2 (1.8), glucose (10), sucrose (30); pH. 7.4. In order to block the voltage-gated sodium currents, 40 nM TTX was added to the recording solution. The intracellular solution contained (in mM): K-gluconate (140), HEPES (20), EGTA (1.1), phosphocreatine (5), MgATP (3), GTP (0.3), MgCl2 (5), and CaCl2 (0.1); pH: 7.2. All test compound and glutamate solutions were made-up in the extracellular solution.

The whole-cell current was measured with patch-clamp amplifier (Axopatch 200B), filtered at 2 kHz, digitized at 5 kHz and recorded on a PC with pClamp 8. The cells were voltage-clamped at −80 mV. Solutions were applied by DAD-12 system. A baseline response for each cell was recorded using a 1 s pulse of 500 µM glutamate dissolved in ECS. Responses to test compound were then determined by application of a 10 s pulse of test compound followed by a 1 s pulse of the same concentration of test compound plus 500 µM glutamate and then 10 s of saline. This pulse sequence was repeated until a stable reading was obtained, or until sufficient data points were measured to allow extrapolation to a calculated maximum change.

The mean value of plateau current between 600 ms to 900 ms after application of glutamate or test compound plus glutamate was calculated and used as the parameter to measure the drug effect. The plateau responses in the presence of varying concentrations of test compound were divided by the baseline response in order to calculate the percentage increase. Compounds are deemed active in this test if, at a test concentration of 3 µM or less, they produce a greater than 100% increase in the value of the steady-state current measured due to application of glutamate alone. The concentration at which the glutamate induced current is increased by 100% is commonly referred to as the EC2x value.

The compound of this invention, 8-cyclopropyl-3-[2-(3-fluorophenyl)ethyl]-7,8-dihydro-3H-[1,3]oxazino[6,5-g][1,2,3]benzotriazine-4,9-dione displayed an EC2x value of 0.1 µM.

V. Administration, Dosages, and Formulation

As noted above, the compound and method of the invention increase AMPA receptor-mediated responses, and are useful for the treatment of hypoglutamatergic conditions. The compound is also useful for treatment of conditions such as impairment of memory or other cognitive functions, brought on by a deficiency in the number or strength of excitatory synapses, or in the number of AMPA receptors. The compound may also be used in the treatment of schizophrenia or schizophreniform behavior resulting from a cortical/striatal imbalance, and in facilitation of learning of behaviors dependent upon AMPA receptors.

In subjects treated with the present compound, pharmaceutical compositions and methods memory or other cognitive functions may be impaired, or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present invention, include those disorders that result from aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compound according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition will be about 0.5 to 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see *Remington's Pharmaceutical Sciences* (17th Ed., Mack Pub. Co., 1985). The composition to be administered will contain a quantity of the selected compound in a pharmaceutically effective amount for effecting increased AMPA receptor currents in a subject.

The following examples illustrate but are not intended in any way to limit the invention. Unless otherwise stated, all temperatures are given in degrees Celsius. Unless otherwise stated, all NMR spectra are $^1$H NMR spectra and were obtained in deuterochloroform or deuterated DMSO as solvent using tetramethylsilane as an internal standard. The name of the example compound conforms to IUPAC nomenclature as provided by the computer software ChemSketch by ACD Labs.

EXAMPLE 1

8-Cyclopropyl-3-[2-(3-fluorophenyl)ethyl]-7,8-dihydro-3H-[1,3]oxazino[6,5-g][1,2,3]-benzotriazine-4,9-dione

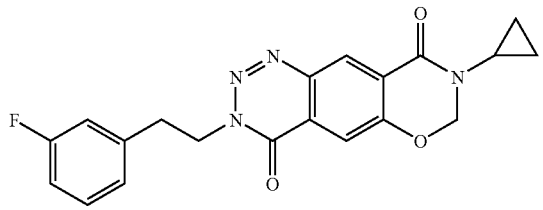

4-Methylsalicylic acid (21.3 g, 140 mmol) was dissolved in methylene chloride (120 mL) followed by CDI (22.7 g, 140 mmol) in portions. The mixture was stirred at room temperature for 24 hr, and then briefly heated to boiling. A solution of cyclopropylamine (8.0 g, 140 mmol) in triethylamine (5 mL, 36 mmol) was added to the mixture, which was stirred for 3 days. Water (200 mL) was added and the pH was adjusted to 2 using 12 M hydrochloric acid. The phases were separated and the aqueous phase was extracted with chloroform (200 mL). The combined organic phases were washed with sodium bicarbonate solution (100 mL) and dried over sodium sulfate. Concentration gave 22.7 g of amide as an off white solid.

The amide (22.7 g, 119 mmol) and trioxane (36 g, 0.4 mol) were dissolved in chloroform (250 mL), which was stirred at room temperature. Sodium sulfate (32 g) and concentrated sulfuric acid (80 drops) were added and the mixture was refluxed for 30 min, after which an additional 40 drops of conc. sulfuric acid were added. After 90 min, the solids were removed by filtration and washed with ethyl acetate. The combined solvents were removed under vacuum to give 30 g of oil. The oil was purified using flash chromatography (250 g silica gel, ethyl acetate:hexane 30:70, then 40:60) to give 20.1 g of 7-methylbenzoxazinone as a colorless oil.

The benzoxazinone (16 g, 79 mmol) was dissolved in methylene chloride (200 mL) to which acetic acid (30 mL) was added. The mixture was cooled to ~0° C. using an ice bath and nitric acid (14 mL, 90%) was added drop wise over 15 min, which produced an orange solution. The reaction mixture was stirred for 90 min and then poured over crushed ice/water (300 mL). A sodium hydroxide solution was slowly added until the pH reached 5. The reaction mixture was extracted with chloroform (200 mL), dried over sodium sulfate and concentrated under vacuum to ~40 mL. Ethyl acetate (200 mL) was added and the mixture was concentrated under vacuum to ~60 mL. The formed crystals were filtered off to give 8.1 g (33 mmol, yield=41%) the desired 6-nitro isomer as an off white solid. The mother liquor was concentrated and more product crystallized (1.2 g) as an off white solid. Subsequently, another 5 g of mixed isomers were isolated from the mother liquor, this mix was used in the following step.

The mixed isomer solids from the previous step (5 g, 20 mmol) were suspended in N,N-dimethylformamide dimethyl acetal (30 mL) and DMF (10 mL) and heated to 125° C. for 16 hr. The solvent was removed under vacuum to yield a dark brown residue. The residue was dissolved in THF (100 mL). Sodium periodate (11 g, 51 mmol) was dissolved in water (100 mL) and added to the reaction mixture, which was stirred for 15 min at room temperature. The beige slurry was extracted with chloroform (200 mL), which was dried over sodium sulfate and diluted with ethyl acetate (200 mL). The solvents were allowed to slowly evaporate, which resulted in the crystallization of the desired isomer (2.0 g, 7.6 mmol) as an off white solid).

The nitro aldehyde intermediate (524 mg, 2.0 mmol) was dissolved in DMF (10 mL) at 40° C. After the solution was cooled to ambient, oxone (1.47 g, 2.4 mmol) was added and the mixture was stirred overnight. Addition of water (25 mL) and ethyl acetate (30 mL) produced two phases, which were separated and the organic phase was filtered and washed with water. The aqueous phase was extracted with ethyl acetate and the combined organic phases were washed twice with water, dried over magnesium sulfate and concentrated under vacuum to give a wet, yellow residue (0.54 g, 1.9 mmol), which was used without further purification.

A solution of the nitro acid intermediate (0.54 g, 1.9 mmol) in methylene chloride was combined with thionyl chloride (1.4 mL, 20 mmol) together with a few drops of DMF stirred at ambient temperature overnight. The mixture was concentrated under vacuum and redissolved in methylene chloride (10 mL). 3-Fluorophenethylamine (0.56 mL, 4.3 mmol) and triethylamine (1.1 mL, 7.9 mmol) were dissolved in methylene chloride (15 mL) to which the freshly prepared solution of the acid chloride was added. After being stirred for 2 hr, the solution was washed with aqueous HCl (1 M) and sat. sodium bicarbonate and dried over magnesium sulfate. The product solution was concentrated under vacuum to give a yellow solid, which was triturated in ethyl acetate to give light beige crystals (0.53 g, 1.3 mmol).

The beige solid from the previous step (0.53 g, 1.3 mmol) was dissolved in a mixture of THF (20 mL) and methanol (20 mL) and added to freshly prepared Zn/Cu reagent (10 g, see below). Formic acid (10 drops) was added and the mixture was stirred at ambient temperature overnight, after which TLC showed completion of the reaction. After addition of DMF (2 mL), the mixture was stirred for 10 min, and then filtered through silica gel (2 cm). The silica was washed with THF/methanol (1:1) and the combined filtrate and wash was concentrated under vacuum. Chloroform was added and evaporated to remove any residual water. DMF (2 mL) and an excess of isoamylnitrite (5 mL) were added and the mixture was stirred for 2.5 hr after which TLC showed the reaction was complete. Addition of diethyl ether (5 mL) caused precipitation of the product, which was washed with ethyl acetate and air dried to give 0.29 g of a yellow solid with the following properties: MP 181-182° C.; $^1$H NMR (300 MHz, CDCl$_3$) δ 8.78 (1H, s), 7.82 (1H, s), 7.3-6.8 (4H, m), 5.33 (2H, s), 4.67 (2H, m) 3.21 (2H, m) 2.76 (1H, m) 1.02 (2H, m) and 0.86 ppm (2H, m).

The Zn/Cu reagent (used above) was freshly prepared in the following manner: Conc. HCl (3 mL) was added to 10 g zinc in 100 mL water during vigorous stirring. The stirring continued for 2 min (clumps start to form), after which the water was decanted off. An additional 100 mL of water was added with vigorous stirring. Any remaining clumps were crushed with a spatula. Conc. HCl (3 mL) was added and the stirring was continued for 2 min. After removing the water by decantation, the solid was washed with an additional 100 mL of water. Water (50 mL) was added to the solid and the stirring was continued while a solution of CuSO$_4$ (300 mg in 50 mL water) was added slowly. After the zinc turned black, the water was removed by decantation. The residue was sequentially washed with methanol (50 mL) and THF (50 mL).

EXAMPLE 2

In Vivo Physiological Testing

The physiological effects of the invention compound were tested in vivo in anesthetized animals according to the following procedures.

Animals are maintained under anesthesia by phenobarbital administered using a Hamilton syringe pump. Stimulating and recording electrodes are inserted into the perforant path and dentate gyrus of the hippocampus, respectively. Once electrodes are implanted, a stable baseline of evoked responses are elicited using single monophasic pulses (100 μs pulse duration) delivered at 3/min to the stimulating electrode. Field EPSPs are monitored until a stable baseline is achieved (about 20-30 min), after which a solution of test compound in HPCD is injected intraperitoneally and evoked field potentials are recorded. Evoked potentials are recorded for approximately 2 h following drug administration or until the amplitude of the field EPSP returns to baseline. In the latter instance, it is common that an iv administration is also carried out with an appropriate dose of the same test compound.

8-cyclopropyl-3-[2-(3-fluorophenyl)ethyl]-7,8-dihydro-3H-[1,3]oxazino[6,5-g][1,2,3]benzotriazine-4,9-dione produced an increase in the amplitude of the field EPSP of 10% at a dose of 5 mg/kg following iv administration.

While the invention has been described with reference to specific methods and embodiments, it will be appreciated that various modifications may be made without departing from the invention.

What is claimed is:

1. A compound of the formula:

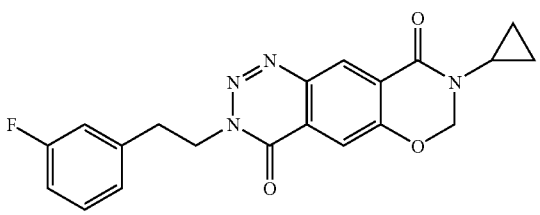

or a pharmaceutically acceptable addition salt of an acid or base thereof.

2. A method for treating a condition selected from schizophrenia, Parkinson's disease, and Alzheimer's disease in a subject in need thereof, said method comprising administering to said subject, in a pharmaceutically acceptable carrier, an effective amount of a compound according to claim 1.

3. The method according to claim 2 wherein said condition is schizophrenia.

4. The method according to claim 2 wherein said condition is Parkinson's disease.

5. The method according to claim 2 wherein said condition is Alzheimer's disease.

6. A pharmaceutical composition comprising an effective amount of a compound according to claim 1 in combination with a pharmaceutically acceptable carrier, additive or excipient.

7. The composition according to claim 6 wherein said compound comprises about 0.5% to about 75% by weight of said composition and said carrier, additive or excipient comprises about 25% to about 95.5% of said composition.

* * * * *